(12) United States Patent
Koizumi et al.

(10) Patent No.: US 6,673,581 B1
(45) Date of Patent: Jan. 6, 2004

(54) MANNOSE ISOMERASE AND DNA ENCODING THE ENZYME

(75) Inventors: Satoshi Koizumi, Machida (JP); Kazuhiko Tabata, Hofu (JP); Tetsuo Endo, Machida (JP); Akio Ozaki, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/958,548

(22) PCT Filed: Apr. 19, 2000

(86) PCT No.: PCT/JP00/02545
§ 371 (c)(1),
(2), (4) Date: Oct. 11, 2001

(87) PCT Pub. No.: WO00/65072
PCT Pub. Date: Nov. 2, 2000

(30) Foreign Application Priority Data

Apr. 22, 1999 (JP) ............................................ 11-114294

(51) Int. Cl.[7] .......................... C12P 19/24; C12P 19/02; C12N 9/90; C12N 1/21; C07H 21/04
(52) U.S. Cl. .......................... 435/94; 435/105; 435/233; 435/252.3; 536/23.2
(58) Field of Search .............................. 435/233, 252.3, 435/320.1, 252.33, 94, 105; 536/23.2

(56) References Cited

U.S. PATENT DOCUMENTS 4,492,755 A    1/1985  Horwath et al. .............. 435/94
5,240,717 A  * 8/1993  Takasaki et al. ............ 435/233

FOREIGN PATENT DOCUMENTS

JP    6-292578    10/1994
JP    8-9986       1/1996

OTHER PUBLICATIONS

Matsudaira (1991) Methods in Enzymology, vol. 182, pp. 602–613.*
Wozney (1991) Methods in Enzymology, vol. 182, pp. 738–751.*
Stevens et al. (1981) J. Gen. Microbiol., vol. 124, pp. 219–223.*
Blattner et al. (1997) Science, vol. 277, pp. 1453–1474.*
Berlyn, "Linkage Map of *Escherchia coli* K–12, Edition 10: The Traditional Map", Microbiol. Mol. Biol., vol. 62, No. 3 (1998), pp. 814, 852, 969.
Stevens,. et al., "Growth on D–Lyxose of a Mutant Strain of *Escherichia coli* K12 . . . ", Journal of General Microbiology (1976), vol. 97, pp. 257–265.
Plunkett, III, et al., "Analysis of *Escherichia coli* genome . . . ", Nucleic Acids Research (1993), vol. 21, No. 15, pp. 3391–3398.

* cited by examiner

*Primary Examiner*—Elizabeth Slobodyansky
(74) *Attorney, Agent, or Firm*—Fitzpatrick, Cella, Harper & Scinto

(57) ABSTRACT

The present invention provides a novel protein having mannose isomerase activity, DNA encoding the protein, a recombinant vector comprising the DNA, a transformant obtained by introducing the recombinant vector into a host cell, and processes for producing the above protein and mannose, fructose, xylulose and lyxose by using the transformant.

4 Claims, 1 Drawing Sheet

SEQUENCE LISTING

```
<160> NUMBER OF SEQ ID NOS: 4

<210> SEQ ID NO 1
<211> LENGTH: 418
<212> TYPE: PRT
<213> ORGANISM: Escherichia coli

<400> SEQUENCE: 1

Met Arg Ile Lys Gly Met Lys Trp Phe Asn Thr Leu Ser His Asn Arg
  1               5                  10                  15

Trp Leu Glu Gln Glu Thr Asp Arg Ile Phe Asp Phe Gly Lys Asn Ser
             20                  25                  30

Val Val Pro Thr Gly Phe Gly Trp Leu Gly Asn Lys Gly Gln Ile Lys
         35                  40                  45

Glu Glu Met Gly Thr His Leu Trp Ile Thr Ala Arg Met Leu His Val
     50                  55                  60

Tyr Ser Val Ala Ala Ala Met Gly Arg Pro Gly Ala Tyr Ser Leu Val
 65                  70                  75                  80

Asp His Gly Ile Lys Ala Met Asn Gly Ala Leu Arg Asp Lys Lys Tyr
                 85                  90                  95

Gly Gly Trp Tyr Ala Cys Val Asn Asp Glu Gly Val Val Asp Ala Ser
            100                 105                 110

Lys Gln Gly Tyr Gln His Phe Phe Ala Leu Leu Gly Ala Ala Ser Ala
        115                 120                 125

Val Thr Thr Gly His Pro Glu Ala Arg Lys Leu Leu Asp Tyr Thr Ile
    130                 135                 140

Glu Ile Ile Glu Lys Tyr Phe Trp Ser Glu Glu Glu Gln Met Cys Leu
145                 150                 155                 160

Glu Ser Trp Asp Glu Ala Phe Ser Lys Thr Glu Glu Tyr Arg Gly Gly
                165                 170                 175

Asn Ala Asn Met His Ala Val Glu Ala Phe Leu Ile Val Tyr Asp Val
            180                 185                 190

Thr His Asp Lys Lys Trp Leu Asp Arg Ala Ile Arg Val Ala Ser Val
        195                 200                 205

Ile Ile His Asp Val Ala Arg Asn Asn His Tyr Arg Val Asn Glu His
```

```
                    210                 215                 220
Phe Asp Thr Gln Trp Asn Pro Leu Pro Asp Tyr Asn Lys Asp Asn Pro
225                 230                 235                 240

Ala His Arg Phe Arg Ala Phe Gly Gly Thr Pro Gly His Trp Ile Glu
                245                 250                 255

Trp Gly Arg Leu Met Leu His Ile His Ala Ala Leu Glu Ala Arg Cys
            260                 265                 270

Glu Gln Pro Pro Ala Trp Leu Leu Glu Asp Ala Lys Gly Leu Phe Asn
        275                 280                 285

Ala Thr Val Arg Asp Ala Trp Ala Pro Asp Gly Ala Asp Gly Ile Val
    290                 295                 300

Tyr Thr Val Asp Trp Glu Gly Lys Pro Val Val Arg Glu Arg Val Arg
305                 310                 315                 320

Trp Pro Ile Val Glu Ala Met Gly Thr Ala Tyr Ala Leu Tyr Thr Val
                325                 330                 335

Thr Gly Asp Arg Gln Tyr Glu Thr Trp Tyr Gln Thr Trp Trp Glu Tyr
                340                 345                 350

Cys Ile Lys Tyr Leu Met Asp Tyr Glu Asn Gly Ser Trp Trp Gln Glu
                355                 360                 365

Leu Asp Ala Asp Asn Lys Val Thr Thr Lys Val Trp Asp Gly Lys Gln
370                 375                 380

Asp Ile Tyr His Leu Leu His Cys Leu Val Ile Pro Arg Ile Pro Leu
385                 390                 395                 400

Ala Pro Gly Met Ala Pro Ala Val Ala Ala Gly Leu Leu Asp Ile Asn
                405                 410                 415

Ala Lys

<210> SEQ ID NO 2
<211> LENGTH: 1254
<212> TYPE: DNA
<213> ORGANISM: Escherichia coli

<400> SEQUENCE: 2
atgaggataa aaggaatgaa atggtttaac accctaagcc acaaccgttg gctggaacag    60
gaaaccgacc gcatctttga ttttggtaaa aattccgtag tgccgactgg ttttggctgg   120
ttaggcaata aagggcaaat caaagaagag atgggcaccc atctgtggat caccgctcgt   180
atgttgcacg tttattccgt tgctgcgggc atgggtcgac ctggcgctta ctcgttggtt   240
gatcacggta tcaaagccat gaacggcgca ctgcgtgata aaaaatatgg cggctggtat   300
gcctgcgtga tgacgagggg cgtggtggat gcctccaaac agggctatca acacttcttt   360
gctctgctgg gtgccgccag cgccgtcaca acgggtcacc cggaagcgcg caagctgctc   420
gattaccaca ttgaaattat cgagaaatat ttctggagcg aagaagagca gatgtgcctg   480
gaatcctggg acgaagcctt cagcaaaacc gaagagtacc gcggcggcaa tgccaatatg   540
cacgcggtgg aagctttctt gattgtttat gacgtcactc acgacaaaaa atggctggat   600
cgcgcgattc gcgtggcttc cgtgattatc cacgacgtcg ccagaaataa tcattatcgc   660
gttaacgaac acttcgatac ccagtggaat ccgctgccgg attacaacaa agataacccg   720
gcgcatcgct tccgcgcgtt cggaggtaca ccaggccact ggatcgaatg ggccgtttta   780
atgctgcaca tccatgctgc cctggaagcc cgttgcgaac aaccaccagc atggctgcta   840
gaagatgcca aaggtctgtt taacgccacc gtgcgcgatg cctgggcacc cgatggcgcg   900
gacgggattg tttataccgt tgactgggaa ggaaaaccgg tggtccgcga acgtgtacgt   960
```

-continued

```
tggcctatcg tcgaagcaat gggtacggcc tacgcgctct acaccgtcac tggcgatcgc    1020
cagtatgaaa cctggtatca aacatggtgg gagtactgca ttaagtacct gatggactat    1080
gaaaatggtt cctggtggca ggagctggat gcggacaata aggtcaccac caaagtctgg    1140
gacggcaaac aggatattta tcacctgctg cattgcctgg tgatcccgcg tatcccgtta    1200
gcgcccggca tggctccagc ggttgcagcg ggtctgctgg atattaatgc gaaa          1254

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ctaatcgatg ctaagatgag gataaaagga atg                                   33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tcaggatcct tatttcgcat taatatccag cag                                   33
```

MANNOSE ISOMERASE AND DNA ENCODING THE ENZYME

TECHNICAL FIELD

The present invention relates to a protein having mannose isomerase activity, DNA encoding the protein, a recombinant DNA comprising the DNA, a transformant carrying the recombinant DNA, a process for producing mannose isomerase by using the transformant, and processes for producing fructose, mannose, xylulose and lyxose by using the transformant.

BACKGROUND ART

Mannose isomerase is known to be present in microorganisms belonging to the genera Pseudomonas [J. Biol. Chem., 218, 535 (1956); Japanese Published Unexamined Patent Application No. 292578/94; U.S. Pat. No. 5,124,262 (1992)], Mycobacterium [J. Bacteriol., 101, 777 (1970)], Xanthomonas [Agric. Biol. Chem., 28, 605 (1964)], Streptomyces [Agric. Biol. Chem., 31, 435 (1967)], Acinetobacter (Japanese Published Unexamined Patent Application No. 9986/96) and Escherichia [J. Gen. Microbiol., 97, 257 (1976)]. However, DNA encoding this enzyme has not yet been isolated from any of these microorganisms.

Mannose isomerase derived from *Escherichia coli* has been purified and its properties have been studied [J. Gen. Microbiol., 124, 219 (1981)], but its amino acid sequence has not been analyzed yet. The nucleotide sequence of the chromosomal DNA of *Escherichia coli* has been determined [Science, 277, 1453 (1997)], and on the basis of the database of Yale University, *E. coli* Genetic Stock Center, the mannose isomerase gene is assumed to be present at around 87.6 minutes on the chromosome. However, the gene has not been specified or isolated.

With regard to the production of carbohydrates by utilizing mannose isomerase, there are known processes for producing mannose by utilizing mannose isomerase derived from a bacterium of the genus Pseudomonas (Japanese Published Unexamined Patent Application No. 292587/94) and mannose isomerase derived from a bacterium of the genus Acinetobacter (Japanese Published Unexamined Patent Application No. 9986/96). These processes, however, require a long reaction time because of low enzyme activity per cell, and thus are not suitable for industrial production of mannose.

So far, no process has been known for efficiently producing carbohydrates by utilizing mannose isomerase.

DISCLOSURE OF THE INVENTION

An object of the present invention is to provide a protein having mannose isomerase activity, DNA encoding the protein, a process for producing a protein having mannose isomerase activity by using the DNA, and efficient processes for producing fructose, mannose, xylulose and lyxose by using the protein.

The present inventors made an intensive investigation to attain the object. As a result, they have succeeded in isolating DNA encoding mannose isomerase from a microorganism belonging to the genus Escherichia, and have found it possible to efficiently produce carbohydrates such as mannose by utilizing the isolated DNA. The present invention has been completed on the basis of this result.

The present invention relates to the following (1)–(14).

(1) A protein consisting of an amino acid sequence wherein one or more amino acid residues are deleted, substituted or added in the amino acid sequence shown in SEQ ID NO: 1 and having mannose isomerase activity. The protein comprising an amino acid sequence wherein one or more amino acid residues are deleted, substituted or added and having mannose isomerase activity can be produced by site-directed mutagenesis described in Molecular Cloning, A Laboratory Manual, Second Edition, Cold Spring Harbor Laboratory Press (1989) (hereinafter referred to as Molecular Cloning, Second Edition); Current Protocols in Molecular Biology, John Wiley & Sons (1987–1997) (hereinafter referred to as Current Protocols in Molecular Biology); Nucleic Acids Research, 10, 6487 (1982); Nucleic Acids Research, 13, 4431 (1985); Proc. Natl. Acad. Sci. USA, 79, 6409 (1982); Proc. Natl. Acad. Sci. USA, 82, 488 (1985); Gene, 34, 315 (1985), etc.

Examples of the proteins produced by the above method are proteins obtained by introducing a site-directed mutation into DNA encoding a protein having the amino acid sequence shown in SEQ ID NO: 1.

The number of amino acid residues which are deleted, substituted or added is not specifically limited, but is preferably within the range of one to several decades, more preferably one to several.

(2) A DNA encoding a protein consisting of the amino acid sequence shown in SEQ ID NO: 1.

(3) A DNA encoding a protein comprising an amino acid sequence wherein one or more amino acid residues are deleted, substituted or added in the amino acid sequence shown in SEQ ID NO: 1 and having mannose isomerase activity.

(4) A DNA having the nucleotide sequence shown in SEQ ID NO: 2.

(5) A DNA which hybridizes to the DNA according to any of the above (2)–(4) under stringent conditions and which encodes a protein having mannose isomerase activity.

The expression "DNA which hybridizes under stringent conditions" as used herein refers to DNA which is obtained by colony hybridization, plaque hybridization, Southern hybridization and so on using the DNA according to any of the above (2)–(4) as a probe. Such DNA can be identified, for example, by performing hybridization at 65° C. in the presence of 0.7–1.0 M NaCl using a filter with colony- or plaque-derived DNA immobilized thereon and then washing the filter at 65° C. using 0.1 to 2-fold concentrated SSC solution (1-fold concentrated SSC solution: 150 mM sodium chloride and 15 mM sodium citrate).

Hybridization can be carried out according to the methods described in laboratory manuals such as Molecular Cloning, Second Edition; Current Protocols in Molecular Biology; and DNA Cloning 1: Core Techniques, A Practical Approach, Second Edition, Oxford University (1995). The hybridizable DNA is, for example, a DNA having at least 80% homology, preferably 95% or more homology to the nucleotide sequence shown in SEQ ID NO: 2.

(6) A recombinant DNA which is obtained by inserting the DNA according to any of the above (2)–(5) into a vector.

(7) A transformant which is obtained by introducing the recombinant DNA according to the above (6) into a host cell.

(8) The transformant according to the above (7) which is *Escherichia coli*.

(9) A process for producing a protein having mannose isomerase activity, which comprises culturing the transformant according to the above (7) or (8) in a medium, allowing the protein having mannose isomerase activity to form and accumulate in the culture, and recovering the protein from the culture.

(10) A process for producing fructose, which comprises allowing a culture of a transformant obtained by introducing DNA encoding a protein having mannose isomerase activity or a treated matter thereof as an enzyme source and mannose to be present in an aqueous medium, allowing fructose to form and accumulate in the aqueous medium, and recovering fructose from the aqueous medium.

(11) A process for producing mannose, which comprises allowing a culture of a transformant obtained by introducing DNA encoding a protein having mannose isomerase activity or a treated matter thereof as an enzyme source and fructose to be present in an aqueous medium, allowing mannose to form and accumulate in the aqueous medium, and recovering mannose from the aqueous medium.

(12) A process for producing xylulose, which comprises allowing a culture of a transformant obtained by introducing DNA encoding a protein having mannose isomerase activity or a treated matter thereof as an enzyme source and lyxose to be present in an aqueous medium, allowing xylulose to form and accumulate in the aqueous medium, and recovering xylulose from the aqueous medium.

(13) A process for producing lyxose, which comprises allowing a culture of a transformant obtained by introducing DNA encoding a protein having mannose isomerase activity or a treated matter thereof as an enzyme source and xylulose to be present in an aqueous medium, allowing lyxose to form and accumulate in the aqueous medium, and recovering lyxose from the aqueous medium.

(14) The process according to any of the above (10)–(13), wherein the transformant is the transformant according to the above (7) or (8).

The present invention is described in detail below.

[1] Preparation of The DNA Encoding Mannose Isomerase

The DNA encoding mannose isomerase can be prepared from a microorganism belonging to the genus Escherichia. Examples of suitable microorganisms belonging to the genus Escherichia are *Escherichia coli, Escherichia blattae, Escherichia fergusonii, Escherichia hermannii, Escherichia intermedia, Escherichia vulneris*, etc. specifically, *Escherichia coli* XL1-Blue, *Escherichiae coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110 (ATCC 27325), *Escherichia coli* NY49, *Escherichia coli* MP347, *Escherichia coli* NM522, *Escherichia blattae* ATCC 33430, *Escherichia fergusonii* ATCC 35473, *Escherichia hermannii* ATCC 33652, *Escherichia intermedia* ATCC 21073, *Escherichia vulneris* ATCC 39368, etc.

According to a known method (e.g., Current Protocols in Molecular Biology), a microorganism belonging to the genus Escherichia is cultured and the chromosomal DNA of the microorganism is isolated and purified.

The nucleotide sequence of the chromosomal DNA of *Escherichia coli* has been determined [Science, 277, 1453 (1997)], and on the basis of the database of Yale University.

*E. coli* Genetic Stock Center, the mannose isomerase gene is assumed to be present at around 87.6 minutes on the chromosome.

On the basis of the above information, a fragment comprising the DNA encoding mannose isomerase derived from a microorganism belonging to the genus Escherichia can be obtained by PCR [PCR Protocols, Academic Press (1990)] using primers prepared based on the nucleotide sequence around 87.6 minutes on the chromosome of *Escherichia coli* and, as a template, a genomic DNA.

The DNA encoding mannose isomerase can also be obtained, for example, by hybridization using a synthetic DNA designed based on the nucleotide sequence of genome as a probe.

The obtained DNA, as such or after cleavage with appropriate restriction enzymes, is inserted into a vector by a conventional method, and then determined a nucleotide sequence of the DNA by a nucleotide sequence analyzing method usually employed, e.g., the dideoxy method [Proc. Natl. Acad. Sci. USA, 74, 5463 (1977)] using 373A DNA Sequencer (Perkin-Elmer Corp.) or the like.

Suitable vectors for the insertion of the above DNA include pBluescript KS+ (Stratagene), pDIRECT [Nucleic Acids Research, 18, 6069 (1990)], pCR-Script Amp SK+ (Stratagene), pT7Blue (Novagen), pCR II (Invitrogen), pCR-TRAP (GenHunter), pNoTA[77] (5Prime→Prime), etc.

An example of the DNA having a nucleotide sequence which is obtained by the above method is the DNA having the nucleotide sequence shown in SEQ ID NO: 2.

One example of an *Escherichia coli* strain carrying a plasmid containing the DNA having the sequence shown in SEQ ID NO: 2 is *Escherichia coli* NM522/pYP27.

The desired DNA can also be prepared by chemical synthesis based on the determined nucleotide sequence of the DNA using a DNA synthesizer (e.g., DNA Synthesizer Model 8905, PerSeptive Biosystems).

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Research, 16, 6127 (1988)].

[2] Preparation of the Protein of the Present Invention

The protein having mannose isomerase activity can be produced by expressing the DNA encoding the protein having mannose isomerase activity and obtained by the method described in [1] above in host cells according to, for example, the following method.

On the basis of the DNA encoding the protein having mannose isomerase activity and obtained by the method described in [1] above, a DNA fragment of an appropriate length comprising a region encoding the protein having mannose isomerase activity is prepared according to need.

Further, DNA useful for improving the production efficiency of the protein having mannose isomerase activity can be prepared by replacing a nucleotide in the nucleotide sequence of the region encoding the protein having mannose isomerase activity so as to make a codon most suitable for the expression in a host cell.

The above DNA fragment or full length DNA is inserted downstream of a promoter region in an appropriate expression vector to construct a recombinant DNA.

Then, the recombinant DNA is introduced into a host cell suited for the expression vector, whereby a transformant which produces the protein having mannose isomerase activity can be obtained.

As the host cell, any procaryotic cells, yeast cells, animal cells, insect cells, plant cells, etc. that are capable of expressing the desired gene can be used. Animals and plants can also be used as hosts.

The expression vectors that can be employed are those capable of autonomous replication or integration into chromosome in the above host cells and comprising a promoter at a position appropriate for the transcription of the DNA encoding the protein having mannose isomerase activity.

When a procaryotic cell such as a bacterial cell is used as the host cell, it is preferred that the expression vector for expressing the above DNA is an expression vector which is capable of autonomous replication in the procaryotic cell and which comprises a promoter, a ribosome binding sequence, the above DNA, and a transcription termination sequence. The vector may further comprise a gene regulating the promoter.

Examples of suitable expression vectors are pBTrp2, pBTac1 and pBTac2 (all available from Boehringer Mannheim), pKK233-2 (Pharmacia), pSE280 (Invitrogen), pGEMEX-1 (Promega), pQE-8 (QIAGEN), pQE-30 (QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK+ (Stratagene), pBluescript II SK− (Stratagene), pTrs30 (FERM BP-5407), pTrs32 (FERM BP-5408), pGHA2 (FERM BP-400), pGKA2 (FERM BP-6798), pTerm2 (Japanese Published Unexamined Patent Application No. 22979/91, U.S. Pat. No. 4,686,191, U.S. Pat. No. 4,939,094, U.S. Pat. No. 5,160,735), pEG400 [J. Bacteriol., 172, 2392 (1990)], pGEX (Pharmacia), pET system (Novagen), pSupex, pUB110, pTP5, pC194, pTrx-Fus (Invitrogen), pMAL-c2 (New England Biolabs), pUC18 [Gene, 33, 103 (1985)], pUC19 [Gene, 33, 103 (1985)], pSTV29 (Takara Shuzo Co., Ltd.), pSTV28 (Takara Shuzo Co., Ltd.), pUC118 (Takara Shuzo Co., Ltd.) and pPA1 (Japanese Published Unexamined Patent Application No. 233798/88).

As the promoter, any promoters capable of functioning in host cells can be used. For example, promoters derived from *Escherichia coli* or phage, such as trp promoter (Ptrp), lac promoter (Plac), PL promoter, PR promoter and PSE promoter, SPO1 promoter, SPO2 promoter and penP promoter can be used. Artificially modified promoters such as a promoter in which two Ptrps are combined in tandem (Ptrp×2), tac promoter, letI promoter, lacT7 promoter and etc. can also be used.

It is preferred to use a plasmid in which the distance between the Shine-Dalgarno sequence (ribosome binding sequence) and the initiation codon is adjusted to an appropriate length (e.g., 6–18 bases).

The transcription termination sequence is not essential for the expression of the desired DNA, but it is preferred that the transcription termination sequence lie immediately downstream of the structural gene.

Examples of suitable host cells are cells of microorganisms belonging to the genera Escherichia, Serratia, Bacillus, Brevibacterium, Corynebacterium, Microbacterium, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus and Zymomonas. Preferred are microorganisms of the genera Escherichia, Bacillus, Brevibacterium, Corynebacterium, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus and Zymomonas.

Specific examples of the above microorganisms are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coil* No. 49, *Escherichia coli* W3110, *Escherichia coli* NY49, *Escherichia coli* MP347, *Escherichia coli* NM522, *Serratia ficaria*, *Serratia fonticola*, *Serratia liquefaciens*, *Serratia marcescens*, *Bacillus subtilis*, *Bacillus amyloliquefaciens*, *Corynebacterium ammoniagenes* ATCC 6872, *Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Brevibacterium divaricatum* ATCC 14020, *Brevibacterium roseum* ATCC 13825, *Brevibacterium thiogenitalis* ATCC 19240, *Corynebacterium glutamicum* ATCC 13032, *Corynebacterium glutamicum* ATCC 14297, *Corynebacterium acetoacidophilum* ATCC 13870, *Corynebacterium acetoglutamicum* ATCC 15806, *Corynebacterium callunae* ATCC 15991, *Corynebacterium lilium* ATCC 15990, *Corynebacterium melassecola* ATCC 17965, *Microbacterium ammoniaphilum* ATCC 15354, Pseudomonas sp. D-0110, *Agrobacterium radiobacter*, *Agrobacterium rhizogenes*, *Agrobacterium rubi*, *Anabaena cylindrica*, *Anabaena doliolum*, *Anabaena flos-aquae*, *Arthrobacter aurescens*, *Arthrobacter citreus*, *Arthrobacter globformis*, *Arthrobacter hydrocarboglutamicus*, *Arthrobacter mysorens*, *Arthrobacter nicotianae*, *Arthrobacter paraffineus*, *Arthrobacter protophormiae*, *Arthrobacter roseoparaffinus*, *Arthrobacter sulfureus*, *Arthrobacter ureafaciens*, *Chromatium buderi*, *Chromatium tepidum*, *Chromatium vinosum*, *Chromatium warmingii*, *Chromatium fluviatile*, *Erwinia uredovora*, *Erwinia carotovora*, *Erwinia ananas*, *Erwinia herbicola*, *Erwinia punctata*, *Erwinia terreus*, *Methylobacterium rhodesianum*, *Methylobacterium extorquens*, Phormidium sp. ATCC 29409, *Rhodobacter capsulatus*, *Rhodobacter sphaeroides*, *Rhodopseudomonas blastica*, *Rhodopseudomonas marina*, *Rhodopseudomonas palustris*, *Rhodospirillum rubrum*, *Rhodospirillum salexigens*, *Rhodospirillum salinarum*, *Streptomyces ambofaciens*, *Streptomyces aureofaciens*, *Streptomyces aureus*, *Streptomyces fungicidicus*, *Streptomyces griseochromogenes*, *Streptomyces griseus*, *Streptomyces lividans*, *Streptomyces olivogriseus*, *Streptomyces rameus*, *Streptomyces tanashiensis*, *Streptomyces vinaceus* and *Zymomonas mobilis*.

Introduction of the recombinant DNA can be carried out by any of the methods for introducing DNA into the above host cells, for example, electroporation [Nucleic Acids Res., 16, 6127 (1988)], the method using calcium ion [Proc. Natl. Acad. Sci. USA, 69, 2110 (1972)], the protoplast method (Japanese Published Unexamined Patent Application No. 248394/88) and the methods described in Gene, 17, 107 (1982) and Molecular & General Genetics, 168, 111 (1979).

When a yeast cell is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast cells can be used. Suitable promoters include PHO5 promoter, PGK promoter, GAP promoter, ADH promoter, gal 1 promoter, gal 10 promoter, heat shock protein promoter, MFα1 promoter, CUP1 promoter, etc.

Examples of suitable host cells are cells of yeast strains belonging to the genera Saccharomyces, Schizosaccharomyces, Kluyveromyces, Trichosporon, Schwanniomyces, Pichia, Candida, etc. specifically, *Saccharomyces cerevisiae, Schizosaccharomyces pombe, Kluyveromyces lactis, Trichosporon pullulans, Schwanniomyces alluvius, Pichia pastoris* and *Candida utilis*.

Introduction of the recombinant DNA can be carried out by any of the methods for introducing DNA into yeast cells, for example, electroporation [Methods in Enzymol., 194, 182 (1990)], the spheroplast method [Proc. Natl. Acad. Sci. USA, 81, 4889 (1984)], the lithium acetate method [J. Bacteriol., 153, 163 (1983)] and the method described in Proc. Natl. Acad. Sci. USA, 75, 1929 (1978).

When an animal cell is used as the host cell, pcDNAI/Amp, pcDNAI and pCDM8 (all available from Funakoshi), pAGE107 [Japanese Published Unexamined Patent Application No. 22979/91; Cytotechnology, 3, 133 (1990)], pREP4 (Invitrogen), pAGE103 [J. Biochem., 101, 1307 (1987)], pAGE210, pAMo, pAMoA [J. Biol. Chem., 268, 22782–22787 (1993), another name: pAMoPRSA (Japanese Published Unexamined Patent Application No. 336963/93)], pAS3-3 (Japanese Published Unexamined Patent Application No. 227075/90), etc. can be used as the expression vector.

As the promoter, any promoters capable of functioning in animal cells can be used. Suitable promoters include the promoter of IE (immediate early) gene of cytomegalovirus (human CMV), SV40 early promoter, the long terminal repeat promoter of moloney murine leukemia virus, the promoter of a retrovirus, heat shock promoter, SRα promoter, metallothionein promoter, etc. The enhancer of IE gene of human CMV may be used in combination with the promoter.

Examples of suitable host cells are mouse myeloma cells, rat myeloma cells, mouse hybridomas, Chinese hamster-derived CHO cells, BHK cells, African green monkey kidney cells, human-derived Namalwa cells and Namalwa KJM-1 cells, human embryonic kidney cells, human leukemia cells, HBT5637 (Japanese Published Unexamined Patent Application No. 299/88) and human large bowel cancer cell strains.

The mouse myeloma cells include SP2/0, NSO, etc.; the rat myeloma cells include YB2/0, etc.; the human embryonic kidney cells include HEK293 (ATCC: CRL-1573), etc.; the human leukemia cells include BALL-1, etc.; the African green monkey kidney cells include COS-1, COS-7, etc.; and the human large bowel cancer cell strains include HCT-15, etc.

Introduction of the recombinant DNA into animal cells can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be expressed by using the methods described in Baculovirus Expression Vectors, A Laboratory Manual, W. H. Freeman and Company, New York (1992); Molecular Biology, A Laboratory Manual; Current Protocols in Molecular Biology, Supplement 1-38; Bio/Technology, 6, 47 (1988), etc.

That is, the recombinant gene transfer vector and a baculovirus are cotransfected into an insect cell to obtain a recombinant virus in the culture supernatant of the insect cell, and then an insect cell is infected with the recombinant virus, whereby the protein can be expressed.

Examples of the gene transfer vectors suitable for use in this method are pVL1392, pVL1393 and pBlueBacIII (products of Invitrogen).

An example of the baculovirus is Autographa californica nuclear polyhedrosis virus, which is a virus infecting insects belonging to the family Barathra.

Examples of the insect cells are ovarian cells of *Spodoptera frugiperda*, ovarian cells of *Trichoplusia ni*, and silkworm ovary-derived cell lines.

The ovarian cells of *Spodoptera frugiperda* include Sf9, Sf21 (Baculovirus Expression Vectors, A Laboratory Manual), etc; the ovarian cells of *Trichoplusia ni* include High 5, BTI-TN-5B1-4 (Invitrogen), etc; and the silkworm ovary-derived cell lines include *Bombyx mori* N4, etc.

Cotransfection of the above recombinant gene transfer vector and the above baculovirus into an insect cell for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

It is also possible to introduce the DNA into an insect cell by the same methods as used for introducing the DNA into an animal cell, for example, electroporation [Cytotechnology, 3, 133 (1990)], the calcium phosphate method (Japanese Published Unexamined Patent Application No. 227075/90) and lipofection [Proc. Natl. Acad. Sci. USA, 84, 7413 (1987)].

When a plant cell or plant is used as the host, the protein can be produced according to known methods [Soshiki Baiyo (Tissue Culture), 20 (1994); Soshiki Baiyo (Tissue Culture), 21 (1995); Trends in Biotechnology, 15, 45 (1997)].

Useful expression vectors include Ti plasmid, tobacco mosaic virus vector, etc.

As the promoter for the gene expression, any promoters capable of functioning in plant cells can be used. Suitable promoters include 35S promoter of cauliflower mosaic virus (CaMV), rice actin 1 promoter, etc. The efficiency of gene expression can be enhanced by inserting intron 1 of the maize alcohol dehydrogenase gene or the like between the promoter and the gene to be expressed.

Examples of suitable host cells are cells of plants such as potato, tobacco, maize, rice, rape, soybean, tomato, carrot, wheat, barley, rye, alfalfa and flax.

Introduction of the recombinant DNA can be carried out by any of the methods for introducing DNA into plant cells, for example, the Agrobacterium method (Japanese Published Unexamined Patent Applications Nos. 140885/84 and 70080/85, WO94/00977), electroporation (Japanese Published Unexamined Patent Application No. 251887/85) and the method using particle gun (gene gun) (Japanese Patents Nos. 2606856 and 2517813).

The plant cells or organs carrying the introduced gene can be subjected to mass culture using a jar fermentor.

Culture media suitable for use in the culturing include generally employed media such as Murashige-Skoog (MS) medium and White medium, and media prepared by adding phytohormones (e.g., auxin and cytokinin) to these media.

Culturing is usually carried out at pH 5–9 at 20–40° C. for 3–60 days.

If necessary, antibiotics such as kanamycin and hygromycin may be added to the medium during the culturing.

Further, it is possible to cause the plant cells carrying the introduced gene to redifferentiate in order to produce a plant having the introtuced gene (transgenic plant).

It is also possible to produce the desired protein using an animal. For example, the desired protein can be produced in an animal carrying the introduced gene according to known methods [American Journal of Clinical Nutrition, 63, 639S (1996); American Journal of Clinical Nutrition, 63, 627S (1996); Bio/Technology, 9, 830 (1991)].

As the promoter, any promoters capable of functioning in an animal can be used. Preferred promoters include mammary gland cell-specific promoters such as α casein promoter, β casein promoter, β lactoglobulin promoter and whey acidic protein promoter.

The desired protein can be produced by culturing the transformant derived from a microorganism, an animal cell or a plant cell carrying the recombinant vector comprising the DNA encoding the protein according to a conventional culturing method, allowing the protein to form and accumulate, and recovering the protein from the culture.

When the transformant is an animal or plant, the protein can be produced by raising or culturing the animal or plant in a usual manner, allowing the protein to form and accumulate therein, and recovering the protein from the animal or plant.

In the case of an animal, the protein having mannose isomerase activity can be produced, for example, by raising a non-human transgenic animal carrying the DNA encoding the protein having mannose isomerase activity, allowing the protein encoded by the recombinant DNA to form and accumulate in the animal, and recovering the protein from the animal. The places where the protein is formed and accumulated include milk, egg, etc. of the animal.

In the case of a plant, the protein having mannose isomerase activity can be produced, for example, by culturing a transgenic plant carrying the DNA encoding the protein having mannose isomerase activity, allowing the protein encoded by the recombinant DNA to form and accumulate in the plant, and recovering the protein from the plant.

When the transformant to be used for the production of the protein having mannose isomerase activity of the present invention is a procaryote such as *Escherihica coli* or a eucaryote such as yeast, the protein having mannose isomerase activity can be produced by culturing the transformant in a medium, allowing the protein having mannose isomerase activity to form and accumulate in the culture, and recovering the protein from the culture.

Culturing of the transformant of the present invention can be carried out by conventional methods for culturing the host of the transformant.

For the culturing of the transformant prepared by using a procaryote such as *Escherichia coli* or a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources which can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of various organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is carried out under aerobic conditions, for example, by shaking culture or submerged spinner culture under aeration, at 15–40° C. usually for 5 hours to 7 days. The pH is maintained at 3.0–9.0 during the culturing. The pH adjustment is carried out by using an organic or inorganic acid, an alkali solution, urea, calcium carbonate, ammonia, etc.

If necessary, antibiotics such as ampicillin, kanamycin and chloramphenicol may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside (IPTG) or the like may be added to the medium; and in the case of a microorganism transformed with an expression vector comprising trp promoter, indoleacrylic acid (IAA) or the like may be added.

For the culturing of the transformant prepared by using an animal cell as the host cell, generally employed media such as RPMI1640 medium [The Journal of the American Medical Association, 199, 519 (1967)], Eagle's MEM [Science, 122, 501 (1952)], DMEM [Virology, 8, 396 (1959)] and 199 medium [Proceeding of the Society for the Biological Medicine, 73, 1 (1950)], media prepared by adding fetal calf serum or the like to these media, etc. can be used as the medium.

Culturing is usually carried out at pH 6–8 at 25–40° C. for 1–7 days in the presence of 5% $CO_2$.

If necessary, antibiotics such as kanamycin, penicillin and streptomycin may be added to the medium during the culturing.

For the culturing of the transformant prepared by using an insect cell as the host cell, generally employed media such as TNM-FH medium (Pharmingen), Sf-900II SFM medium (Gibco BRL), ExCell 400 and ExCell 405 (JRH Biosciences) and Grace's Insect Medium [Grace, T. C. C., Nature, 195, 788 (1962)] can be used as the medium.

Culturing is usually carried out at pH 6–7 at 25–30° C. for 1–5 days.

If necessary, antibiotics such as gentamicin may be added to the medium during the culturing.

The full length protein having mannose isomerase activity described above or a partial polypeptide containing the region having the activity of the protein having mannose isomerase activity (catalytic domain) can be expressed directly or as a secretory protein or fusion protein according to the methods described in Molecular Cloning, Second Edition, etc. Examples of the proteins to be fused include β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescence protein, and any antibody epitope [Akio Yamakawa, Jikken Igaku (Experimental Medicine), 13, 469–474 (1995)].

The protein having mannose isomerase activity may be produced intracellularly, secreted extracellularly or produced on outer membranes of host cells. Such production methods can be selected depending on the kind of the host cells used or on alteration of the structure of the protein having mannose isomerase activity to be produced.

When the protein having mannose isomerase activity is produced in host cells or on outer membranes of host cells, it is possible to force the protein having mannose isomerase activity to be secreted extracellularly according to the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, extracellular secretion of the protein having mannose isomerase activity by host cells can be caused by expressing it in the form of a protein in which a signal peptide is added upstream of a polypeptide containing the active site of the protein having mannose isomerase activity by the use of recombinant DNA techniques. Further, a tag for purification and detection can also be added between the signal peptide and the polypeptide containing the catalytic domain or to the C-terminus of the polypeptide containing the catalytic domain.

Suitable tags for purification and detection include β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescence protein, and any antibody epitope [Akio Yamakawa, Jikken Igaku (Experimental Medicine), 13, 469–474 (1995)].

It is also possible to increase the protein production by utilizing a gene amplification system using a dihydrofolate reductase gene or the like according to the method described in Japanese Published Unexamined Patent Application No. 227075/90.

The polypeptide of the present invention can be isolated and purified from a culture of the transformant for the production of the protein having mannose isomerase activity by conventional methods for isolating and purifying enzymes.

For example, when the protein having mannose isomerase activity is accumulated in a soluble form in the transformant cells, the cells are recovered from the culture by centrifugation and washed, followed by disruption using a sonicator, French press, Manton Gaulin homogenizer, Dynomill or the like to obtain a cell-free extract.

A purified protein preparation can be obtained by centrifuging the cell-free extract to obtain the supernatant and then subjecting the supernatant to extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Kasei Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, electrophoresis such as isoelectric focusing, or the like.

When the protein having mannose isomerase activity is expressed as an inclusion body in cells, the cells are similarly recovered and disrupted, followed by centrifugation to obtain a precipitate fraction. After the protein having mannose isomerase activity is recovered from the precipitate fraction by an ordinary method, the inclusion body of the protein having mannose isomerase activity is solubilized with a protein-denaturing agent. The solubilized protein solution is diluted with or dialyzed against a solution containing no protein-denaturing agent or a solution containing the protein-denaturing agent at such a low concentration that denaturation of protein is not caused, whereby the normal tertiary structure of the protein having mannose isomerase activity is restored. Then, a purified protein preparation can be obtained by the same isolation and purification steps as mentioned above.

When the protein having mannose isomerase activity is extracellularly secreted, the culture is treated by means such as centrifugation to give a soluble fraction. A purified preparation of the protein having mannose isomerase activity can be obtained from the soluble fraction in the same manner as in the above isolation and purification from the supernatant of the cell-free extract.

It is also possible to produce the polypeptide of the present invention as a fusion protein with another protein and to purify it by affinity chromatography using a substance having affinity for the fused protein [Akio Yamakawa, Jikken Igaku (Experimental Medicine), 13, 469–474 (1995)].

For example, according to the method of Lowe, et al. [Proc. Natl. Acad. Sci. USA, 86, 8227 (1989); Genes Develop., 4, 1288 (1990)] and the methods described in Japanese Published Unexamined Patent Application No. 336963/93 and WO94/23021, the protein having mannose isomerase activity can be produced as a fusion protein with protein A and can be purified by affinity a chromatography using immunoglobulin G.

Further, it is possible to produce the protein having mannose isomerase activity as a fusion protein with a FLAG peptide and to purify it by affinity chromatography using anti-FLAG antibody [Proc. Natl. Acad. Sci. USA, 86, 8227 (1989); Genes Develop., 4, 1288 (1990)].

The protein having mannose isomerase activity can also be purified by affinity chromatography using an antibody against said protein itself.

The polypeptide of the present invention can also be produced by using an in vitro transcription-translation system according to known methods [J. Biomolecular NMR, 6, 129 (1995); Science, 242, 1162 (1988); J. Biochem., 110, 166 (1991)].

On the basis of the amino acid information on the protein having mannose isomerase activity obtained as above, the protein having mannose isomerase activity can be produced by chemical synthetic methods such as the Fmoc method (the fluorenylmethyloxycarbonyl method) and the tBoc method (the t-butyloxycarbonyl method).

Further, the protein can be chemically synthesized by using peptide synthesizers from Advanced ChemTech, Perkin-Elmer, Pharmacia Biotech, Protein Technology Instrument, Synthecell-Vega, Perseptive, Shimadzu Corporation, etc.

[3] Production of Fructose, Mannose, Xylulose and Lyxose

The culture of the transformant obtained by the culturing described in [2] above or treated matters thereof can be used as an enzyme source for the production of fructose, mannose, xylulose and lyxose in an aqueous medium respectively(hereinafter sometimes referred to as the production of the present invention).

The treated matters of the culture include concentrated culture, dried culture, cells obtained by centrifuging the culture, products obtained by treating the cells by various means such as drying, freeze-drying, treatment with a surfactant, ultrasonication, mechanical friction, treatment with a solvent, enzymatic treatment, protein fractionation and immobilization, an enzyme preparation obtained by extracting the cells, etc.

In the production of the present invention, the enzyme source is used at a concentration of 1 mU/l–1000 U/l, preferably 10 mU/l–100 U/l, one unit (U) being defined as the activity which forms 1 millimole of fructose, mannose, xylulose or lyxose at 37° C. in one minute.

Aqueous media useful in the production of the present invention include water, buffers such as phosphate buffer, carbonate buffer, acetate buffer, borate buffer, citrate buffer and Tris buffer, alcohols such as methanol and ethanol, esters such as ethyl acetate, ketones such as acetone, amides such as acetamide, etc. The culture of the microorganism used as the enzyme source can be used also as the aqueous medium.

If necessary, a surfactant or an organic solvent may be added in the production of the present invention. Any surfactant that promotes the formation of fructose, mannose, xylulose or lyxose can be used. Suitable surfactants include nonionic surfactants such as polyoxyethylene octadecylamine (e.g., Nymeen S-215, NOF Corporation), cationic surfactants such as cetyltrimethylammonium bromide and alkyldimethyl benzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation), which may be used alone or in combination. The surfactant is usually used at a concentration of 0.1–50 g/l. As the organic solvent, xylene, toluene, aliphatic alcohols, acetone, ethyl acetate, etc. may be used usually at a concentration of 0.1–50 ml/l.

Reaction for the production of the present invention is carried out in an aqueous medium at pH 5–10, preferably pH 6–8, at 20–60° C. for 1–96 hours. If necessary, an inorganic salt (e.g., $MgCl_2$), etc. may be added in the reaction.

Determination of fructose, mannose, xylulose and lyxose formed in the aqueous medium can be carried out by using a carbohydrate analysis system (Dionex) or the like [Anal. Biochem., 189, 151 (1990)].

Recovery of fructose, mannose, xylulose and lyxose formed in the reaction mixture can be carried out by ordinary methods using active carbon, ion-exchange resins, etc.

BEST MODES FOR CARRYING OUT THE INVENTION

Figure 1:
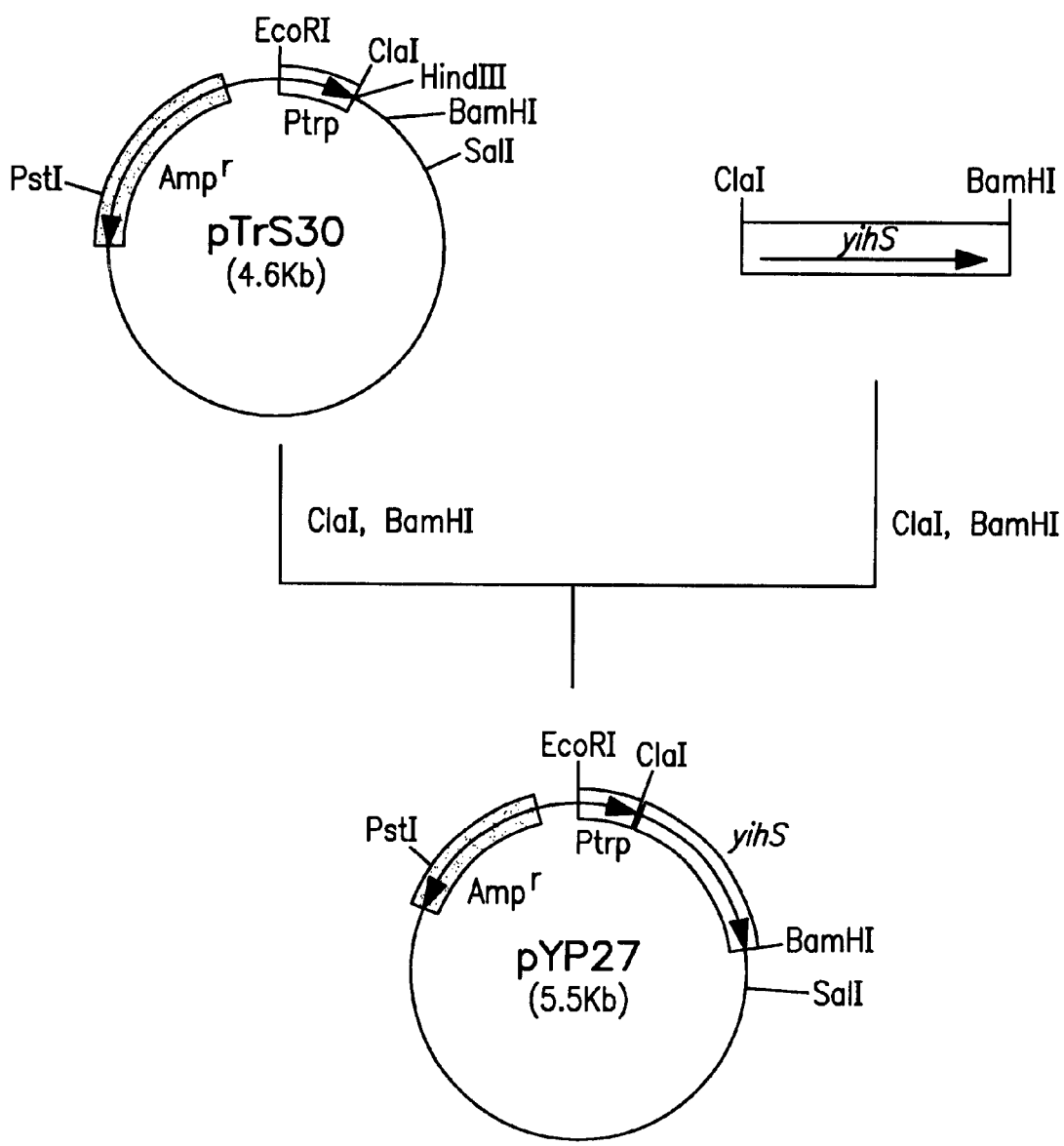
FIG. 1 shows the steps for constructing plasmid pYP27 expressing mannose isomerase. In the figure, $Amp^r$ represents ampicillin resistance gene, Ptrp represents tryptophan promoter, and yihS represents mannose isomerase gene.

Examples of the present invention are shown below. These examples are not to be construed as limiting the scope of the invention.

EXAMPLE 1

Construction of a Strain Expressing DNA Encoding a Protein Having Mannose Isomerase Activity Derived from *Escherichia coli*.

*Escherichia coli* W3110 (ATCC 27325) was cultured by a known method [e.g., Current Protocols in Molecular Biology, John Wiley & Sons (1987–1997)] and its chromosomal DNA was isolated and purified.

A DNA primer having the nucleotide sequence shown in SEQ ID NO: 3 and a DNA primer having the nucleotide sequence shown in SEQ ID NO: 4 were synthesized using a DNA synthesizer (Model 8905, PerSeptive Biosystems) on the basis of the information on the known nucleotide sequence of the chromosomal DNA of *Escherichia coli* [Science, 277, 1453 (1997)], the information on the location of mannose isomerase gene on the chromosome assumed by Yale University and the information that a gene of unknown function is present at the position of 87.7 minutes on the chromosome of *Escherichia coli*.

PCR was carried out using the above synthetic DNAs as a set of primers and the chromosomal DNA of *Escherichia coli* W3110 as a template.

That is, PCR was carried out by 30 cycles, one cycle consisting of reaction at 94° C. for one minute, reaction at 42° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase (Stratagene), 4 μl of buffer for Pfu DNA polymerase (10-fold) (Stratagene) and 200 μmol/l each of deoxyNTPs.

One-tenth of the resulting reaction mixture was subjected to agarose gel electrophoresis to confirm that the DNA fragment based on the primers used was amplified. Then, the remaining reaction mixture was mixed with an equal amount of phenol/chloroform (1 vol/1 vol) saturated with TE [10 mmol/l Tris-HCl (pH 8.0), 1 mmol/l EDTA].

The resulting mixture was centrifuged and the obtained upper layer was mixed with a two-fold volume of cold ethanol and allowed to stand at −80° C. for 30 minutes.

The resulting mixture was centrifuged to obtain a DNA precipitate.

The DNA precipitate was dissolved in 20 μl of TE and 5 μl of the solution was subjected to reaction to cleave the DNA with restriction enzymes ClaI and BamHI. DNA fragments were separated by agarose gel electrophoresis and a 1.3 kb fragment was recovered using Gene Clean II Kit. pTrS30 DNA (0.2 μg) was cleaved with restriction enzymes ClaI and BamHI. DNA fragments were separated by agarose gel electrophoresis and a 4.2 kb fragment was recovered in the same manner.

The 1.3 kb fragment and 4.2 kb fragment obtained above were subjected to ligation reaction using a ligation kit at 16° C. for 16 hours. *Escherichia coli* NM522 was transformed using the ligation mixture according to the known method described above, spread on LB agar medium containing 50 μg/ml ampicillin, and cultured overnight at 30° C.

A plasmid was extracted from a colony of the transformant that grew on the medium according to the known method described above, whereby expression plasmid pYP27 was obtained. The structure of the obtained plasmid was confirmed by digestion with restriction enzymes (FIG. 1). The transformant carrying this plasmid is hereinafter referred to as *Escherichia coli* NM522/pYP27.

EXAMPLE 2

Production of Mannose, Fructose, Xylulose and Lyxose

*Escherichia coli* NM522/pYP27 obtained in Example 1 was inoculated into 8 ml of LB medium containing 50 μg/ml ampicillin in a large test tube, and cultured at 28° C. for 17 hours.

The resulting culture was inoculated into 8 ml of M9 medium containing 50 μg/ml ampicillin in a large test tube in an amount of 1%, and cultured at 37° C. for 7 hours.

The resulting culture was centrifuged to obtain wet cells.

The wet cells could be stored at −20° C. and could be used after thawing, according to need.

Reaction mixtures were prepared by adding 100 mmol/l fructose for the production of mannose, 100 mmol/l mannose for the production of fructose, 100 mmol/l lyxose for the production of xylulose and 100 mmol/l xylulose for the production of lyxose, respectively, to a solution comprising 100 mmol/l Tris-HCl (pH 7.5), 50 mmol/l MgCl$_2$ and 0.4% Nymeen S-215.

To 0.1 ml of each of the prepared reaction mixtures was added the wet cells obtained above to give the final concentration of 60 mg/ml, followed by reaction at 37° C. for one hour.

After the completion of reaction, the reaction products were analyzed by using a carbohydrate analysis system (DX-500, Dionex).

It was found that 21.9 mmol/l mannose, 74.4 mmol/l fructose, 70.4 mmol/l xylulose and 24.4 mmol/l lyxose were formed and accumulated in the respective reaction mixtures.

None of the carbohydrates were formed by the use of *Escherichia coli* NM522/pTrS30 carrying only the vector.

Industrial Applicability

According to the present invention, mannose isomerase can be produced in large amounts by recombinant DNA techniques. Mannose, fructose, xylulose and lyxose can be efficiently produced by the use of the enzyme.

[Sequence Listing Free Text]

SEQ ID NO: 3—Description of the artificial sequence: synthetic DNA

SEQ ID NO: 4—Description of the artificial sequence: synthetic DNA

What is claimed is:

1. A process for producing fructose, which comprises:
preparing an aqueous medium comprising mannose and an enzyme source comprising a culture of a transformant obtained by introducing into a host a DNA selected from the group consisting of a DNA encoding a protein consisting of the amino acid sequence shown in SEQ ID NO: 1, a DNA consisting of the nucleotide sequence shown in SEQ ID NO: 2, and a DNA which hybridizes to the DNA consisting of the nucleotide sequence shown in SEQ ID NO: 2 under stringent conditions, wherein said stringent conditions comprise hybridization at 65° C. using the filter with colony- or plaque-derived DNA immobilized thereon and then washing the filter at 65° C. using 0.1 to 2-fold concentrated SSC solution (1-fold concentrated SSC solution being 150 mM sodium chloride and 15 mM sodium citrate), and encodes a protein having mannose isomerase activity, or a treated matter of the culture selected from the group consisting of concentrated culture, dried culture, cells obtained by centrifuging the culture, products obtained from the cells by drying, freeze-drying, treatment with a surfactant, ultrasonication, mechanical friction, treatment with a solvent, enzymatic treatment, protein fractionation or immobilization, or an enzyme preparation obtained by extracting the cells, wherein said treated matter retains said mannose isomerase activity,
allowing fructose to form and accumulate in the aqueous medium, and
recovering fructose from the aqueous medium.

2. A process for producing mannose, which comprises:
preparing an aqueous medium comprising fructose and an enzyme source comprising a culture of a transformant obtained by introducing into a host a DNA selected from the group consisting of a DNA encoding a protein consisting of the amino acid sequence shown in SEQ ID NO: 1, a DNA consisting of the nucleotide sequence shown in SEQ ID NO: 2, and a DNA which hybridizes to the DNA consisting of the nucleotide sequence shown in SEQ ID NO: 2 under stringent conditions, wherein said stringent conditions comprise hybridization at 65° C. using the filter with colony- or plaque-derived DNA immobilized thereon and then washing the filter at 65° C. using 0.1 to 2-fold concentrated SSC solution (1-fold concentrated SSC solution being 150 mM sodium chloride and 15 mM sodium citrate), and encodes a protein having mannose isomerase activity, or a treated matter of the culture selected from the group consisting of concentrated culture, dried culture, cells obtained by centrifuging the culture, products obtained from the cells by drying, freeze-drying, treatment with a surfactant, ultrasonication, mechanical friction, treatment with a solvent, enzymatic treatment, protein fractionation or immobilization, or an enzyme preparation obtained by extracting the cells, wherein said treated matter retains said mannose isomerase activity,
allowing mannose to form and accumulate in the aqueous medium, and
recovering mannose from the aqueous medium.

3. A process for producing xylulose, which comprises:
preparing an aqueous medium comprising lyxose and an enzyme source comprising a culture of a transformant obtained by introducing into a host a DNA selected from the group consisting of a DNA encoding a protein consisting of the amino acid sequence shown in SEQ ID NO: 1, a DNA consisting of the nucleotide sequence shown in SEQ ID NO: 2, and a DNA which hybridizes to the DNA consisting of the nucleotide sequence shown in SEQ ID NO: 2 under stringent conditions, wherein said stringent conditions comprise hybridization at 65° C. using the filter with colony- or plaque-derived DNA immobilized thereon and then washing the filter at 65° C. using 0.1 to 2-fold concentrated SSC solution (1-fold concentrated SSC solution being 150 mM sodium chloride and 15 mM sodium citrate), and encodes a protein having mannose isomerase activity, or a treated matter of the culture selected from the group consisting of concentrated culture, dried culture, cells obtained by centrifuging the culture, products obtained from the cells by drying, freeze-drying, treatment with a surfactant, ultrasonication, mechanical friction, treatment with a solvent, enzymatic treatment, protein fractionation or immobilization, or an enzyme preparation obtained by extracting the cells, wherein said treated matter retains said mannose isomerase activity, allowing xylulose to form and accumulate in the aqueous medium, and recovering xylulose from the aqueous medium.

4. A process for producing lyxose, which comprises:

preparing an aqueous medium comprising xylulose and an enzyme source comprising a culture of a transformant obtained by introducing into a host a DNA selected from the group consisting of a DNA encoding a protein consisting of the amino acid sequence shown in SEQ ID NO: 1, a DNA consisting of the nucleotide sequence shown in SEQ ID NO: 2, and a DNA which hybridizes to the DNA consisting of the nucleotide sequence shown in SEQ ID NO: 2 under stringent conditions, wherein said stringent conditions comprise hybridization at 65° C. using the filter with colony- or plaque-derived DNA immobilized thereon and then washing the filter at 65° C. using 0.1 to 2-fold concentrated SSC solution (1-fold concentrated SSC solution being 150 mM sodium chloride and 15 mM sodium citrate), and encodes a protein having mannose isomerase activity, or a treated matter of the culture selected from the group consisting of concentrated culture, dried culture, cells obtained by centrifuging the culture, products obtained from the cells by drying, freeze-drying, treatment with a surfactant, ultrasonication, mechanical friction, treatment with a solvent, enzymatic treatment, protein fractionation or immobilization, or an enzyme preparation obtained by extracting the cells, wherein said treated matter retains said mannose isomerase activity, allowing lyxose to form and accumulate in the aqueous medium, and recovering lyxose from the aqueous medium.

* * * * *